United States Patent [19]

Nohara et al.

[11] Patent Number: 4,714,774
[45] Date of Patent: Dec. 22, 1987

[54] BENZOIC ACID DERIVATIVES AND THEIR PRODUCTION

[75] Inventors: Akira Nohara; Yoshitaka Maki, both of Kyoto, Japan

[73] Assignee: Takeda Chemical Industries, Ltd., Osaka, Japan

[21] Appl. No.: 791,543

[22] Filed: Oct. 25, 1985

[30] Foreign Application Priority Data

Oct. 30, 1984 [WO] PCT Int'l Appl. ... PCT/JP84/00520
Sep. 25, 1985 [JP] Japan ................................ 60-213578

[51] Int. Cl.$^4$ ............................................. C07C 69/76
[52] U.S. Cl. .................................. 560/053; 560/255;
514/543; 562/463
[58] Field of Search ................. 560/053, 255; 514/546,
514/543; 562/463

[56] References Cited

FOREIGN PATENT DOCUMENTS 28063 6/1981 European Pat. Off. .
80371 1/1983 European Pat. Off. .
123541 10/1984 European Pat. Off. .

Primary Examiner—Paul J. Killos
Attorney, Agent, or Firm—Wegner & Bretschneider

[57] ABSTRACT

A benzoic acid derivative of the formula:

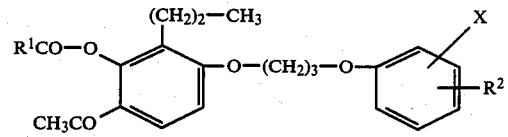

wherein $R^1$ stands for a lower alkyl group, $R^2$ stands for an optionally protected carboxyl group and X stands for a halogen or a salt thereof, has excellent antiasthmatic and antiinflammatory activities and therefore is useful as an antiasthmatic or antiinflammatory agent for a mammalian animal.

11 Claims, No Drawings

BENZOIC ACID DERIVATIVES AND THEIR PRODUCTION

This invention relates to benzoic acid derivatives or salts thereof exhibiting an antagonistic action on the slow reacting substance of anaphylaxis (SRS-A), which is a group of chemical mediators, which induce a contraction of bronchial and other smooth muscles and which are useful as among others, antiasthmatic agents, and to a method for producing them.

As compounds exhibiting an antagonistic action on SRS-A, which is a group of chemical mediators, which induce a contraction of bronchial smooth muscle, there may be mentioned those disclosed in British Patent Application Publication No. 1,384,530, European Patent Application Publication No. 28,063 and European Patent Application Publication No. 80,371.

However, an antagonistic action of those compounds on SRS-A specifically disclosed in working examples of the British Patent Application Publication No. 1,384,530 and European Patent Application Publication No. 28,063 can hardly be satisfactory and an improvement of the action has been desired. As to the compound disclosed in European Patent Application Publication No. 80,371, an improvement in oral absorbability and increasing the durability of action have been desired.

The present inventors have diligently conducted research work aiming at obtaining a compound which has a satisfactory antagonistic action on SRS-A, and found that a certain group of benzoic acid derivatives meet the purpose. This finding was followed by further studies, on which the present invention has been predicated.

Thus, the present invention relates to
(1) a benzoic acid derivative (I) of the formula;

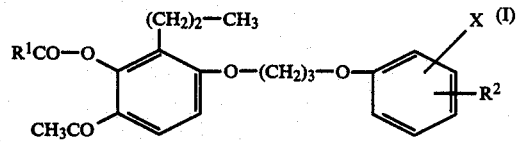

wherein $R^1$ stands for a lower alkyl group, $R^2$ stands for an optionally protected carboxyl group and X stands for a halogen atom or a salt thereof, (2) a method for producing a benzoic acid derivative (I) or a salt thereof, which comprises allowing a compound (II) of the formula:

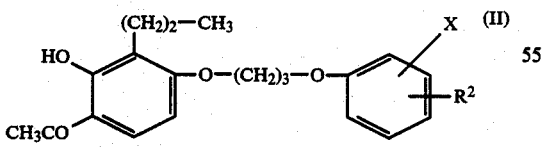

wherein $R^2$ and X are of the same meaning as defined above or a salt thereof to react with an acylating agent (V) of the formula:

wherein $R^1$ is of the same meaning as defined above and Y stands for a leaving group when the compound is acylated, (3) a method for producing a benzoic acid derivative (III) of the formula:

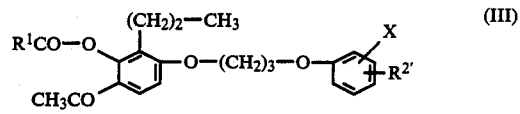

wherein $R^1$ and X are of the same meaning as defined above and $R^{2'}$ stands for a protected carboxyl group or a salt thereof, which comprises subjecting a compound (IV) of the formula:

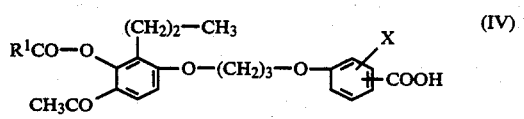

wherein $R^1$ and X are of the same meaning as defined above or a salt thereof to a reaction for introducing a protective group of the carboxyl group, (4) a method for producing a benzoic acid derivatives (IV) or a salt thereof, which comprises subjecting a compound (I") of the formula:

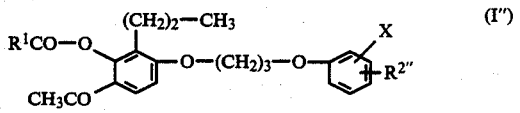

wherein $R^1$ and X are of the same meaning as defined above and $R^{2''}$ stands for carboxyl group protected by a protective group $(R^{5'})$ to a reaction for removing the protective group $(R^{5'})$, (5) a method for producing a benzoic acid derivative (IV) or a salt thereof, which comprises subjecting a compound of the formula:

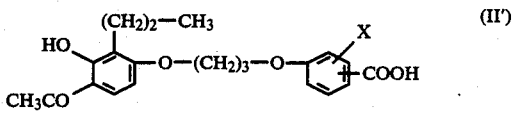

wherein X is of the same meaning as defined above or a salt thereof to a reaction for introducing a protective group $(R^{5'})$ of the carboxyl group to give a compound of the formula:

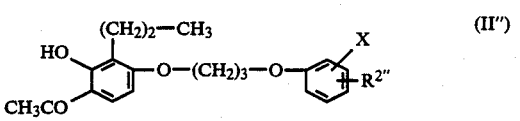

wherein $R^{2''}$ and X are of the same meanings as defined above, allowing the compound (II") to react with an acylating agent of the formula (V) to give a compound of the formula:

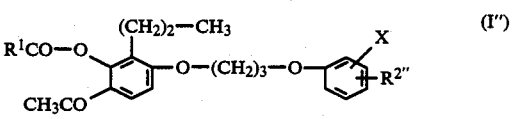

wherein $R^1$, $R^{2''}$ and X are of the same meaning as defined above, then subjecting thus obtained compound to a reaction for removing the protective group ($R^{5'}$), (6) a pharmaceutical composition for antagonizing the slow reacting substance of anaphylaxis which contains an effective antagonizing dose of a compound (I) and a pharmaceutically acceptable carrier, and (7) a method for antagonizing the slow reacting substance of anaphylaxis by administration to a mammal in need thereof of a compound (I).

In the above formulae, as the lower alkyl group shown by $R^1$, those having 1 to 3 carbon atoms are preferable, which are exemplified by methyl, ethyl, n-propyl and isopropyl. Among them are especially preferable methyl and ethyl. The protective group of an optionally protected carboxyl group shown by $R^2$ or that of a protected carboxyl group shown by $R^{2'}$ is represented by $R^5$, which is exemplified by a group shown by the formula

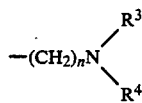 (VI)

[wherein n denotes an integer of 2 to 4, $R^3$ and $R^4$ independently stand for hydrogen or $C_{1-3}$ alkyl, and $R^3$ and $R^4$, taken together with the adjacent nitrogen atom, may form a 5- or 6-membered heterocyclic ring], tetrahydropyranyl, t-butyl, trityl, benzyl, benzyloxymethyl and phenacyl. Among them is preferable the group shown by the formula (VI). The protective group ($R^{5'}$) of a protected carboxyl group shown by $R^{2''}$ is a group other than those shown by the formula

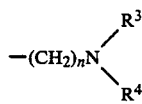

[wherein n, $R^3$ and $R^4$ are of the same meaning as defined above], which is exemplified by tetrahydropyranyl, t-butyl, trityl, benzyl, benzyloxymethyl, phenacyl, etc.

The $C_{1-3}$ alkyl group shown by $R^3$ and $R^4$ in the above formula (VI) is exemplified by methyl, ethyl, n-propyl and isopropyl. The 5- or 6-membered heterocyclic group is exemplified by morpholino, piperazino, piperidino and pyrrolidino. These heterocyclic groups may optionally be substituted by one, two or three substituents. The substituents are exemplified by $C_{1-3}$ lower alkyls (e.g. methyl, ethyl, n-propyl and isopropyl), $C_{1-3}$ lower alkoxy (e.g. methoxy, ethoxy and propoxy), $C_{1-3}$ acyl (e.g. formyl, acetyl and propionyl) and halogen (e.g. chlorine, bromine, iodine and fluorine).

As the halogen shown by X in the above formulae are mentioned bromine, chlorine, fluorine and iodine. As the leaving group when the compound is subjected to acylation, which is shown by Y, are mentioned acyloxy groups e.g. acetoxy, propionyloxy, etc. or halogen atoms e.g. chlorine, bromine etc.

In the above formulae, —X takes preferably ortho-position, while —COOH, —$R^2$, —$R^{2'}$ and —$R^{2''}$ take preferably para-position, respectively. p In the reaction for preparing a compound (I) or a salt thereof by allowing a compound (II) or a salt thereof to react with an acylating agent (V), about 2 to 30 equivalents of the acylating agent (V) is employed relative to one equivalent of the compound (II). The reaction is preferably conducted in the presence of a base such as pyridine, 4-dimethylaminopyridine, triethylamine, etc. The solvent to be employed is exemplified by chloroform, dichloromethane, dimethylformamide, tetrahydrofuran, dioxane, etc., and, in general, an excess amount of pyridine etc. is employed taking a role of the solvent as well. The reaction time ranges from about 1 to 48 hours. The reaction temperature usually ranges from that under ice-cooling to about the boiling points of the reagents and solvents then employed.

The reaction for preparing a compound (III) by subjecting a compound (IV) to a reaction of introducing a protective group of the carboxyl group can be conducted by allowing a halogenating agent to react with the compound (IV) or its salt to give an acid halogenide of the compound (IV), then by allowing the acid halogenide to react with an alcohol derivative of the protective group.

An acid halogenide of a compound (IV) can be produced by allowing a halogenating agent (e.g. thionyl chloride, phosphoryl chloride, thionyl bromide, phosphorus pentachloride, phosphorus trichloride, phosphorus oxychloride, phosphorus tribromide, etc.) to react with a compound (IV). The solvent employable for the reaction is exemplified by chloroform, dichloromethane, dimethylformamide, tetrahydrofuran, dioxane, etc. The reaction temperature ranges from about 80° C. to about 120° C. The reaction time is in the range of from about 0.5 to about 4 hours.

As the alcohol derivative of the protective group in the above-mentioned reaction is mentioned a compound (VII) of the formula:

wherein $R^5$ is of the same meaning as defined above. For the reaction of the above-mentioned acid halogenide with the alcohol derivative (VII), about 1 to 4 equivalents of the latter is employed relative to one equivalent of the former. The solvent to be employed is exemplified by acetone, chloroform, dichloromethane, tetrahydrofuran, dioxane, acetonitrile, etc. The reaction is conducted preferably in the presence of a base. The base is exemplified by triethylamine, pyridine, 4-dimethylaminopyridine, dimethylaniline, etc. The reaction temperature is in the range of about 15° to 80° C., and the reaction time is in the range of about 1 to 10 hours.

The reaction for preparing a compound (III) by subjecting a compound (IV) to a reaction of introducing a protective group of the carboxyl group can be conducted by allowing a halogenide of the protective group to react with the compound (IV).

As a preferable example of the halogenide of the protective group may be mentioned a compound (VIII) of the formula;

wherein Z stands for a halogen atom and $R^5$ is of the same meaning as defined above. The halogen atom shown by Z is exemplified by chlorine, bromine, iodine, etc.

The amount of the compound (VIII) in the above reaction is about 1 to 4 equivalents relative to one equivalent of the compound (IV). The reaction is conducted preferably in the presence of a base such as triethylamine, pyridine, dimethylaniline, etc. For the reaction is employed a solvent such as dimethylformamide, hexamethylphosphoric triamide, tetrahydrofuran, dioxane, acetonitrile, etc. The reaction temperature is in the range of about 70° to 150° C., and the reaction time is about 1 to 6 hours.

In the reaction for preparing a compound (II″) starting from a compound (II′), when $R^{5'}$ is for example tetrahydropyranyl group, dihydropyran of about 1 to 5 equivalents relative to one equivalent of the compound (II′) is employed, and the reaction is allowed to proceed at temperatures within the range of from those under ice-cooling to room temperatures in the presence of a catalylic amount of an acid for about 10 minutes to 5 hours to give the compound (II′). The solvent to be employed is exemplified by methylene chloride, chloroform, acetonitrile, tetrahydrofuran, etc., and the acid is exemplified by p-toluenesulfonic acid, sulfuric acid, etc. When $R^{5'}$ is a benzyl group or t-butyl group, a compound (II′) is made into an acid halogenide by a reaction similar to the above where a compound (IV) is made into an acid halogenide, then the acid halogenide is allowed to react with benzyl alcohol or t-butyl alcohol to give the compound (II″).

When $R^{5'}$ is a trityl group or benzyloxy methyl group, a compound (II′) is first made into a salt of sodium, potassium or silver, etc., and the salt is allowed to react with e.g. trityl bromide or benzyloxymethyl chloride to give the compound (II′). When $R^{5'}$ is a phenacyl group, e.g. phenacyl bromide is allowed to react with a ccmpound (II′) in the presence of e.g. triethylamine to give the compound (II″). The solvent to be employed for the reaction is exemplified by benzene, hexane, chloroform, dichloromethane, ethyl acetate, tetrahydrofuran, acetonitrile, etc.

For any of the above-mentioned reactions, the reaction temperature may be adequately chosen from those under ice-cooling to those about the boiling point of the solvent then employed, and the reaction time ranges from about 1 to about 5 hours.

The reaction for preparing a compound (I″) from a compound (II″) thus produced as above can be conducted by a process similar to the acylation which comprises allowing the afore-mentioned compound (II) to react with the compound (V) to give the compound (I).

In the reaction for preparing a compound (IV) by removing the protective group $R^{5'}$ from the group $R^{2''}$ of the compound (I″), reactions for removing $R^{5'}$ vary with the kinds of the protective group $R^{5'}$. For example, when $R^{5'}$ is a tetrahydropyranyl group, the reaction is conducted in e.g. tetrahydrofuran-water or acetic acid in the presence of an acid e.g. hydrochloric acid, p-toluenesulfonic acid, etc. around room temperatures for about 30 minutes to 5 hours. When $R^{5'}$ is benzyloxymethyl or phenacyl, the reaction can be conducted by means of catalytic reduction using e.g. palladium as the catalyst at about room temperatures for about 1 to 10 hours. When $R^{5'}$ is t-butyl or trityl, the reaction can be conducted in the presence of an acid e.g. hydrochloric acid, trifluoroacetic acid, formic acid, p-toluenesulfonic acid, etc. at temperatures ranging from those under ice-cooling to about 50° C. for about 1 to 5 hours.

The end-products prepared by the above-mentioned processes can be separated from reaction mixtures and purified by a per se known process e.g. recrystallization, chromatography, etc.

The salts of the starting compounds and end-products of this invention are preferably those which are pharmacologically acceptable, which are exemplified by alkali metal salts such as sodium salt or potassium salt, and inorganic or organic acid salts such as hydrochloride, sulfate, phosphate, fumarate, maleate or oxalate.

The starting compound (II) of the method of the present invention where $R^2$ is carboxyl group can be prepared by the method described in the European Patent Application Publication No. 80,371 or by a method analogous thereto.

Among the compounds (I) according to this invention, those where $R^2$ stands for —COOH or a compound of the formula

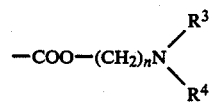

hereinafter referred to as compound (I′) exhibit a remarkable antagonistic action on the slow reacting substance of anaphylaxis (SRS-A), which is a group of chemical mediators, which induces a contraction of bronchial and other smooth muscles.

SRS-A is produced by various stimuli such as immune reactions and has been considered to be a potent mediator of bronchospasm in immediate allergy such as allergic asthma. SRS-A consists of leukotriene C(LTC), leukotriene D(LTD), etc., and it is known that LTD and LTC are substantially equivalent in activity on the human bronchial muscle and that LTD is superior to LTC in constrictive effect on the guinea pig ileum [S. E. Dahlen et al., Nature 288, 484 (1980); R. A. Lewis et al., Biochemical and Biophysical Research Communications 96, 271 (1980)]. The antagonistic effect of drugs against SRS-A can be investigated using the guinea pig ileum [R. A. Appleton et al., Journal of Medicinal Chemistry 20, 371 (1977)] and since SRS-A is a mixture of LTC, LTD, etc. and the ratio thereof is indefinite, it is desirable to use a synthetic SRS-A in the investigation of antagonistic activity.

The present inventors studied the antagonistic action of compound (I) against SRS-A using a synthetic $LTD_4$ in the following manner, and found that, against the bronchoconstriction in guinea pigs due to an intravenous administration of synthetic leukotriene $D_4$ ($LTD_4$), certain species of the compounds (I′) when administered orally one hour before $LTD_4$ dosing displayed a remarkable inhibitory effect superior to the control compound (A).

(1) Test method

Guinea pigs of Hartley strain, both male and female, with body weights about 400 g were assigned to groups of 6 to 10 individuals, and the bronchoconstriction due to $LTD_4$ was measured according to the method of Konzett-Rössler [Konzett, H. and Rössler, R.: Naunyn-Schmiedebergs Archiv für Experimentelle Pathologie und Pharmakologie 195, 71–74 (1940)]. Each guinea pig was fixed in supine position under urethane anesthesia (1.5 g/kg, intraperitoneal) and the trachea was incised and connected to an artificial respiration apparatus, Rodent Respirator Model 680 [Harvard Apparatus Company, U.S.A.] via a cannula. The branch tube of this tracheal cannula was connected to Bronchospasm Transducer Model 7020 [Ugobasil Biological Researach Apparatus, Italy]. Under the conditions of 4 to 7 ml of air per stroke, 70 strokes per minute and a lung loading pressure of 10 $cmH_2O$, the volume of overflowing air was recorded on Rectigraph-8S (San-ei Sokki Co. Ltd., Japan) via a transducer. After administration of gallamine.triethiodide (1 mg/kg, i.v.), a solution of $LTD_4$ in physiological saline (10 μg/kg) was intravenously administered and the bronchoconstriction elicited thereby was recorded for 15 minutes. The compound was used as suspended in a 5% solution of gum arabic or dissolved in water, and administered orally in a volume of 0.2 ml per 100 g body weight one hour before $LTD_4$ loading. $LTD_4$ was administered through a cannula inserted into the jugular vein. $LTD_4$ was used as dissolved in physiological saline, which was taken from a stock stored in methanol (1 mg/1 ml methanol) at −70° C.

(2) Result

| Compound (I') | $R^1CO-$ | $R^2$ | $X^{*1}$ | $ID_{50}$(p.o.) (μmol/kg) |
|---|---|---|---|---|
| (I')-1*2 | $CH_3CO-$ | $-COOH$ | Br | 47 |
| Control (A)*3 compound | H— | $-COOH$ | Br | 146 |

*1$ID_{50}$ (50% inhibitory dose): Each value was calculated from the relation between dosage and the inhibition rate of the overflow volume (in percentage) from the respiratory tract at the time when the response was maximal, i.e. 30 seconds after the administration of $LTD_4$.
*2Compound (I')-1: The compound prepared in Example 1 below.
*3Control compound (A): The compound disclosed in the specification of European Patent Application Publication No. 80,371, shown by the formula;

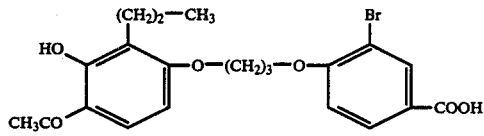

The acute toxicity of compound (I')-1 in mice was found to be as follows.

(1) Method

Five 5-week-old male mice per group, of Jcl:ICR strain, weighing about 30 g each, were used. Compound (I')-1 was suspended in a 5% solution of gum arabic and administered orally at the level of 0.2 ml per 10 grams body weight.

(2) Results

The oral administration of compound (I')-1 in a dose of 500 mg/kg caused no symptoms that could be attributable to compound (I')-1. Autopsy after 7 days did not reveal any abnormalities.

From the foregoing, the toxicity of compound (I') is considered to be low.

It will thus be apparent that the compound (I') is useful in the treatment of diseases due to SRS-A, such as asthma, hay fever, chronic bronchitis, allergic diseases of the eye, allergic diseases of the stomach and intestines, cardiovascular disturbances, allergic dermatitis and other inflammatory diseases. For example, as an antiasthmatic or antiinflammatory drug, the compound (I') or salts thereof can be administered orally or parenterally to mammalian animals (e.g. mouse, rat, guinea pig, man) in a daily dose of about 1 to 20 mg/kg.

For oral administration, the compound (I') or salts thereof can be formulated with a pharmaceutically acceptable carrier, excipient or diluent (e.g. lactose, starch, cellulose derivatives, stearic acid, magnesium stearate, sucrose, gelatin, gum arabic) and processed into such dosage forms as tablets, capsules, granules, troches, liquid, syrup, etc. For parenteral administration, the compound (I') or salts thereof can be formulated with pharmacologically acceptable vehicles, excipients or diluents (e.g. white petrolatum, hydrophilic ointment bases, oleaginous bases, glyceride, polyethylene glycol, etc.) and processed into ointments, suppositories, aerosols, inhalants, injections, etc. These dosage forms may be produced by the established pharmaceutical procedures.

The compound (I) of the present invention, wherein $R^2$ is a carboxyl group ($R^{2''}$) protected with a group ($R^{5'}$) other than protecting groups of the formula

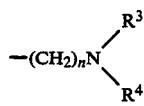

wherein n, $R^3$ and $R^4$ are of the same meaning as defined above [the compound (I'')] is useful as an intermediate for synthesizing the above-mentioned compound (I') useful as an antiasthmatic drug.

The following Reference Examples and Examples illustrate the present invention in more detail.

REFERENCE EXAMPLE 1

By a procedure analogous to that described in the specification of European Patent Application Publication No. 80,371, the following compounds were prepared.

(1) 3-[3-(4-acetyl-3-hydroxy-2-propylphenoxy)-propoxy]-4-bromobenzoic acid methyl ester, m.p. 108°–110° C. (Recrystallization solvent: acetone-ether).

(2) 3-[3-(4-acetyl-3-hydroxy-2-propylphenoxy)-propoxy]-4-bromobenzoic acid, m.p. 146°–149° C. (Recrystallization solvent: aqueous alcohol).

REFERENCE EXAMPLE 2

By a procedure analogous to that described in the specification of European Patent Application Laid-Open No. 80,371, the following compounds were prepared.

(1) 2-[3-(4-acetyl-3-hydroxy-2-propylphenoxy)-propoxy]-5-bromobenzoic acid methyl ester, m.p. 71°–73° C. (Recrystallization solvent: acetone-ether).

(2) 2-[3-(4-acetyl-3-hydroxy-2-propylphenoxy)-propoxy]-5-bromobenzoic acid, m.p. 157°–158° C. (Recrystallization solvent: aqueous alcohol).

REFERENCE EXAMPLE 3

(1) A mixture of 3-fluoro-4-hydroxybenzoic acid (1.2 g), ethanol (20 ml) and concentrated sulfuric acid (1 ml) was refluxed for 13 hours, then concentrated and extracted with chloroform. The extract was washed with aqueous sodium hydrogen carbonate solution, dried and the solvent was distilled off, whereby crystals of ethyl 3-fluoro-4-hydroxybenzoate (1.3 g) was obtained. m.p. 79°–80° C.

(2) A mixture of ethyl 3-fluoro-4-hydroxybenzoate (600 mg), 4-(3-chloropropoxy)-2-hydroxy-3-propylacetophenone (1.15 g), potassium carbonate (450 mg), potassium iodide (550 mg) and dimethylformamide (2 ml) was stirred well for 4.5 hours at 80° to 90° C. To the reaction mixture was added ethyl acetate, and the insolubles were removed off by filtration. The filtrate was subjected to concentration and then the residue was recrystallized from methanol to give crystals of ethyl 4-[3-(4-acetyl-3-hydroxy-2-propylphenoxy)propoxy]-3-fluorobenzoate (1.3 g). m.p. 87°–88° C.

(3) A mixture of ethyl 4-[3-(4-acetyl-3-hydroxy-2-propylphenoxy)-propoxy]-3-fluorobenzoate (1.3 g), ethanol (8 ml) and sodium hydroxide (1 g) in water (5 ml) was refluxed for 40 minutes. Ethanol was distilled off from the reaction mixture. The residue was dissolved in water, and the solution was acidified with diluted hydrochloric acid to give crystals. Recrystallization from ethanol gave crystals (1.06 g) of 4-[3-(4-acetyl-3-hydroxy-2-propylphenoxy-propoxy]-3-fluorobenzoic acid. m.p. 165°-166° C.

(4) A solution of 4-[3-(4-acetyl-3-hydroxy-2-propylphenoxy)propoxy]-3-fluorobenzoic acid (220 mg) in chloroform (2 ml) and thionyl chloride (0.4 ml) was refluxed for 20 minutes, then the solvent was removed under reduced pressure. To the residue was added toluene, and then the solvent was removed under reduced pressure. To the residue thus obtained was added acetone (5 ml), 3-dimethylaminopropanol (70 mg) and triethylamine (0.25 ml), and the mixture was refluxed for 0.5 hour. The precipitated colorless crystals were removed by filtration, and the filtrate was concentrated. The residue was dissolved in chloroform, and the solution was washed once with a saturated sodium hydrogen carbonate, and dried with sodium sulfate. The solvent was removed by evaporation and to the cooled residue was added hexane to give colorless crystals of 3-dimethylaminopropyl 4-[3-(4-acetyl-3-hydroxy-2-propylphenoxy)propoxy]-3-fluorobenzoate (140 mg). m.p. 55°-56° C.

EXAMPLE 1

In a mixture of pyridine (10 ml) and acetic anhydride (10 ml) was dissolved 4-[3-(4-acetyl-3-hydroxy-2-propylphenoxy)propoxy]-3-bromobenzoic acid (2 g). The solution was heated at 100° to 120° C. for 14 hours, which was then concentrated. The residue was dissolved in chloroform. The solution was washed with dilute hydrochloride acid, which was then dried on sodium sulfate. From the resultant was removed the solvent by evaporation, and the residue was chromatographed on a column of silica gel. Elution was conducted with hexane-ethyl acetate (3:1), (2:1), (1:1) and ethyl acetate in that order. Ethyl acetate fractions were combined and concentrated. The residue was crystallized from chloroform-hexane to give 4-[3-(3-acetoxy-4-acetyl-2-propylphenoxy)propoxy]-3-bromobenzoic acid (1.0 g), m.p. 155°-156° C.

By the procedure above was prepared 2-[(3-acetoxy-4-acetyl-2-propylphenoxy)propoxy]-5-bromobenzoic acid, m.p. 125°-127° C. (Recrystallization solvent: acetone-ether).

EXAMPLE 2

A mixture of 4-[3-(4-acetyl-3-hydroxy-2-propylphenoxy)propoxy]-3-bromobenzoic acid (2.0 g), pyridine (10 ml) and propionic anhydride (10 ml) was heated at 100° to 110° C. for about 30 hours, then the solvent was evaporated off. The residue was dissolved in chloroform, which was washed with dilute hydrochloric acid, then with water. The solution was dried (sodium sulfate), which was then chromatographed on a column of silica-gel. The elution was conducted with chloroform-ethylacetate ester (5:1). The eluate was evaporated and the residue was recrystallized from hexane to give 1.77 g of 4-[3-(4-acetyl-3-propionyloxy-2-propylphenoxy)propoxy]-3-bromobenzoic acid, m.p. 136°-137° C.

EXAMPLE 3

(1) A mixture of 4-[3-(4-acetyl-3-hydroxy-2-propylphenoxy]-3-bromobenzoic acid (2 g), chloroform (20 ml) and thionyl chloride (5 ml) was refluxed for 30 minutes, then chloroform was evaporated off. The residue was dissolved in acetone (40 ml). To the solution were added 3-(N,N-dimethylamino)-1-propanol (500 mg) and triethylamine (4 ml). The mixture was stirred at room temperature for two hours. The resulting precipitates were filtered off, and the filtrate was concentrated. The residue was chromatographed on a column of silica gel. Elution was conducted with ethyl acetate and then with ethyl acetate-triethyl amine (10:1). From the eluate was evaporated off the solvent. The residue was recrystallized from hexane to give crystals of 3-(N,N-dimethylamino)propyl 4-[3-(4-acetyl-3-hydroxy-2-propylphenoxy)propoxy]-3-bromobenzoate (1.8 g), m.p. 71°-72° C.

(2) In a mixture of pyridine (5 ml) and acetic anhydride (5 ml) was dissolved 3-(N,N-dimethylamino)propyl 4-[3-(4-acetyl-3-hydroxy-2-propylphenoxy)propoxy]-3-bromobenzoate (1 g). The solution was stirred at 110° to 120° C. for about 18 hours, followed by concentration. The residue was chromatographed on a column of silica gel. The elution was conducted with ethyl acetate, and the eluate was evaporated. The resulting oily substance was dissolved in ether, to which was added an ether solution of anhydrous oxalic acid. The resultant crystals were collected by filtration, which were washed with ethanol and then with isopropyl ether, followed by drying to give 866 mg of 3-(N,N-dimethyl-amino)propyl 4-[3-(4-acetyl-3-acetoxy-2-propylphenoxy)propoxy]-3-bromobenzoate.mono-oxalate, m.p. 141°-142° C.

EXAMPLE 4

(1) In methylene chloride (30 ml) was dissolved 4-[3-(4-acetyl-3-hydroxy-2-propylphenoxy)propoxy]-3-bromobenzoic acid (1.35 g). To the solution were added dihydropyran (0.9 ml) and p-toluene sulfonic acid.-monohydrate (5 mg). The mixture was stirred at room temperature for 30 minutes, to which was further added methylene chloride (30 ml). The resulting solution was washed with an aqueous solution of sodium hydrogen carbonate and then with water, followed by drying with sodium sulfate. The solvent was evaporated off, and the residue was purified by means of a silica-gel column chromatography (Developing solvent: chloroform) to give 1.4 g of tetrahydropyranyl 4-[3-(4-acetyl-3-hydroxy-2-propylphenoxy)propoxy]-3-bromobenzoate as colorless oily substance.

NMR(CDCl$_3$)δ: 0.88(3H,t), 2.38(2H,m), 2.53(3H,s), 2.62(2H,t), 3.7-4.1(2H,m), 4.29(4H,t), 6.18(1H,s), 6.47(1H,d,j=9 Hz), 6.91(1H,d,j=8 Hz), 7.54(1H,d,j=9 Hz), 8.00(1H,dd,j=2 and 8 Hz), 8.23(1H,d,j=2 Hz)

(2) In methylene chloride (20 ml) was dissolved tetrahydropyranyl 4-[3-(4-acetyl-3-hydroxy-2-propylphenoxy)propoxy]-3-bromobenzoate (1.4 g). To the solution were added triethylamine (6 ml) and 4-dimethylaminopyridine (15 mg), to which was added dropwise acetic anhydride (5 ml) under ice-cooling. The mixture was stirred for 30 minutes under ice-cooling, and there was added methanol (5 ml). The mixture was left standing for a while, and there was added chloroform (50 ml). The mixture was washed with a 5% aqueous solution of sodium hydrogen carbonate and then with water, followed by drying (sodium sulfate). The solvent was evaporated off and the residue was purified by means of a silica-gel column-chromatography to give 3 g of tetrahydropyranyl 4-[3-(3-acetoxy-4-acetyl-2-propylphenoxy)propoxy]-3-bromobenzoate as colorless oily substance.

NMR(CDCl$_3$)δ: 0.87(3H,t), 2.34(3H,s), 2.47(3H,s), 4.29(4H,t), 6.18(1H,brs), 6.79(1H,d,j=9 Hz), 6.90(1H,d,j=8 Hz), 7.68(1H,d,j=9 Hz), 7.99(1H,dd,j=2 and 8 Hz), 8.23(1H,d,j=2 Hz)

(3) In tetrahydrofuran (10 ml) was dissolved tetrahydropyranyl 4-[3-(3-acetoxy-4-acetyl-2-propylphenoxy)propoxy]-3-bromobenzoate (1.3 g). To the solution was added 1N HCl (1 ml), which was left standing at room temperature for one hour, followed by addition of chloroform (60 ml). The mixture was washed with water sufficiently and dried with sodium sulfate. Then, the solvent was evaporated off. The residue was crystallized with isopropyl ether, followed by recrystallization from aqueous alcohol to give 0.7 g of 4-[3-(3-acetoxy-4-acetyl-2-propylphenoxy)propoxy]-3-bromobenzoic acid as crystals, m.p. 155°–156° C.

(4) By a procedure analogous to the above (1) to (3) was prepared 3-[3-(3-acetoxy-4-acetyl-2-propylphenoxy)propoxy]-propoxy] -4-bromobenzoic acid, m.p. 137°–139° C. (Recrystallization solvent: aqueous alcohol)

EXAMPLE 5

To a solution of 3-dimethylaminopropyl 4-[3-(4-acetyl-3-hydroxy-2-propylphenoxy)propoxy]-3-fluorobenzoate (124 mg) in dichloromethane (1 ml), triethylamine (0.5 ml) and 4-dimethylaminopyridine (a catalytic amount) was added acetic anhydride (0.38 ml). The mixture was stirred well for 1.5 hours at room temperature. To the reaction mixture was added methanol (2 ml), and the solvents removed by evaporation under reduced pressure. The residue was dissolved in chloroform, the solution was washed with a solution of saturated sodium hydrogen carbonate and dried with sodium sulfate, and the solvent was removed by evaporation. The residue was dissolved in ether, and to the solution was added a saturated solution of oxalic acid in ether until a precipitate did not emerge any more. The precipitate was recovered by filtration and washed with ether to give a white solid of 3-dimethylaminopropyl 4-[3-(3-acetoxy-4-acetyl-2-propylphenoxy)propoxy]-3-fluorobenzoate.mono-oxalate (180 mg). M.p. 166°–167° C.

EXAMPLE 6

To a solution of 4-[3-(4-acetyl-3-hydroxy-2-propylphenoxy)propoxy]-3-chlorobenzoic acid (1.0 g), which was prepared by the manner described in European Patent Application Publication No. 80,371, triethylamine (4.6 ml), 4-dimethylaminopyridine (8 mg) and dichloromethane (6 ml) was added acetic anhydride (3.1 ml) at 5° to 7° C., and the mixture was stirred well for 80 minutes. To the reaction mixture was added dropwise methanol (5 ml) to decompose the excess amount of acetic anhydride. The mixture was subjected to concentration, the residual oily product was poured into ice-water, and the precipitate was collected by filtration. Recrystallization from ethanol-water gave white crystals of 4-[3-(3-acetoxy-4-acetyl-2-propylphenoxy)propoxy]-3-chlorobenzoic acid 975 mg). M.p. 146°–148° C.

EXAMPLE 7

(1) To a solution of 4-[3-(4-acetyl-3-hydroxy-2-propylphenoxy)propoxy]-3-bromobenzoic acid (903 mg) in dichloromethane (100 ml) was added conc. sulfuric acid (five drops), and then into the mixture was bubbled isobutene under ice-cooling for 30 minutes. The mixture was left standing at room temperature for 2 days in a sealed vessel. To the reaction mixture was added sodium hydrogen carbonate, and then was bubbled nitrogen gas to remove isobutene. The insolubles were removed by filtration, and the filtrate was subjected to concentration under reduced pressure. The residue was dissolved in ethyl acetate, the solution was washed with a saturated aqueous solution of sodium hydrogen carbonate, and dried with magnesium sulfate. The solvent was removed by evaporation under reduced pressure and the residue was subjected to purification with silica gel flash chromatography [hexane-ethyl acetate (9:1)]. The eluate was concentrated under reduced pressure to give tertbutyl 4-[3-(4-acetyl-3-hydroxy-2-propylphenoxy)propoxy]-3-bromobenzoate (660 mg) as slightly brown oily product.

NMR (CDCl$_3$)δ: 0.90 (3H, t, J=7 Hz), 1.29–1.72 (2H, m), 1.56 (9H, s), 2.21–2.74 (4H, m), 2.54 (3H, s), 4.28 (2H, t, J=6 Hz), 4.30 (2H, t, J=6 Hz), 6.48 (1H, d, J=9 Hz), 6.88 (1H, d, J=8 Hz), 7.57 (1H, d, J=9 Hz), 7.90 (1H, dd, J=2 and 8 Hz), 8.14 (1H, d, J=2 Hz), 12.72 (1H, s).

(2) Tert-butyl 4-[3-(4-acetyl-3-hydroxy-2-propylphenoxy)propoxy]-3-bromobenzoate (660 mg) was treated in a manner analogous to Example 5 to give tert-butyl 4-[3-(3-acetoxy-4-acetyl-2-propylphenoxy)propoxy]-3-bromobenzoate (610 mg) as slightly brown oily product.

NMR (CDCl$_3$) δ: 0.88 (3H, t, J=7 Hz), 1.32–1.70 (2H, m), 1.57 (9H, s), 2.20–2.65 (4H, m), 2.33 (3H, s), 2.45 (3H, s), 4.13–4.40 (4H, m), 6.78 (1H, d, J=9 Hz), 6.86 (1H, d, J=8 Hz), 7.67 (1H, d, J=9 Hz), 7.88 (1H, dd, J=2 and 8 Hz), 8.13 (1H, d, J=2 Hz).

(3) To a solution of tert-butyl 4-[3-(3-acetoxy-4-acetyl-2-propylphenoxy)propoxy]-3-bromobenzoate (1.5 g) in dioxane (10 ml) was added a cooled solution of 2 N hydrogen chloride in dioxane (10 ml) at 20° C. under stirring. The reaction mixture was warmed to room temperature, and stirred for 30 minutes. To the mixture was added an additional cooled solution of 2 N hydrogen chloride in dioxane (10 ml). The mixture was stirred for 1.5 hours and subjected to concentration under reduced pressure. The residue was dissolved in chloroform (30 ml), and the solution was washed with water (30 ml) and dried with magnesium sulfate. The solvent was removed by evaporation, and the residue was dissolved in isopropyl ether. The solution was treated with activated carbon, and to the solution was added hexane to give crystals. The crystals were collected by filtration, subjected to silica gel column chromatography, and subjected to recrystallization from aqueous ethanol to give colorless crystals of 4-[3-(3-acetoxy-4-acetyl-2-propylphenoxy)propoxy]-3-bromobenzoic acid (0.35 g). M.p. 154°–156° C.

EXAMPLE 8

A mixture of 3-[3-(3-acetoxy-4-acetyl-2-propylphenoxy)propoxy]-3-bromobenzoic acid (200 mg), chloroform (2 ml), and thionyl chloride (0.4 ml) was refluxed for 20 minutes, and concentrated. Toluene was added to the residue followed by evaporation. To the residue were added acetone (5 ml) and 3-dimethylaminopropanol (300 mg) and the mixture was refluxed for 0.5 hour. Precipitates were removed by filtration, and the filtrate was concentrated. The residue was purified by silica gel column chromatography and the eluted oil was dissolved in ether. To the solution was added a solution of oxalic acid to give 200 mg of 3-dimethylaminopropyl 4-[3-(3-acetoxy-4-acetyl-2-propylphenoxy)propoxy]-3-bromobenzoate.mono-oxalate. M.p. 141°–142° C.

EXAMPLE 9

(1) A mixture of 2,4-dihydroxy-3-propylacetophenone (2.7 g), 1,3-dibromopropane (2.8 ml) and potassium carbonate (1.9 g) in acetone (50 ml) was refluxed for 3 hours. Insoluble materials were filtered off, and the filtrate was concentrated. The resulting syrup was purified by means of a silica gel flash chromatography (chloroform-hexane=1:1) to give 3-(4-acetyl-3-hydroxy-2-propylphenoxy)propyl bromide (2.9 g) as colorless and transparent syrup.

NMR(CDCl$_3$)δ: 0.92(3H,t,j=7 Hz), 1.30–1.70(2H,m), 2.33 (2H,m), 2.54(3H,s), 2.63(2H,t,j=6 Hz), 3.60(2H,t,6 Hz), 4.18 (2H,t,j=6 Hz), 6.43(1H,d,j=9 Hz), 7.55(1H,d,9 Hz)

(2) In methylene chloride were dissolved 3-(4-acetyl-3-hydroxy-2-propylphenoxy)propyl bromide (2.8 g), triethylamine (6.2 ml) and dimethylaminopyridine (10 mg). To the solution was added dropwise acetic anhydride (4.2 ml) under ice-cooing. The reaction was allowed to proceed for 3 hours, and there was added methanol (5 ml). The mixture was left standing for 10 minutes. The solvent was evaporated off to leave syrup, which was dissolved in chloroform. The solution was washed with water, dried and concentrated. The resulting syrup was purified by means of a silica gel flash chromatography (chloroform) to give 3-(3-acetoxy-4-acetyl 2-propylphenoxy)propyl bromide (2.7 g) as colorless and transparent syrup.

NMR (CDCl$_3$)δ: 0.93(3H,t,j=7 Hz), 1.30–1.70(2H,m), 2.36 (3H,s), 2.50(3H,s), 2.20~2.70(4H,m), 3.59(2H,t,j=6 Hz), 4.29(2H,t,j=6 Hz), 6.79(1H,d,j=9 Hz), 7.71(1H,d,j=9 Hz)

(3) A mixture of 3-(3-acetoxy-4-acetyl-2-propylphenoxy)propyl bromide(2.3 g), 3-bromo-4-hydroxybenzaldehyde (1.29 g), potassium iodide (1.07 g) and potassium carbonate (0.89 g) in dimethylformamide (30 ml) was heated at 70°–80° C. for 1.5 hour under stirring. To the reaction mixture was added chloroform (100 ml), and insoluble materials were filtered off. The filtrate was washed with water, dried and concentrated to give brownish syrup, which was purified by means of a silica gel flash chromatography. Thus purified syrup was treated with isopropyl ether to cause crystallization. The crystals were recrystallized from aqueous alcohol to give 4-[3-(3-acetoxy-4-acetyl-2-propylphenoxy)propoxy]-3-bromcbenzaldehyde (2.28 g) as pale yellow crystals, m.p. 120°–121° C.

(4) To a solution of 4-[3-(3-acetoxy-4-acetyl-2-propylphenoxy)propoxy]3-bromobenzaldehyde (2.39 g) in acetone (50 ml) was added acetic acid (50 ml). To the well stirred mixture was added pulverized potassium permanganate (1.58 g) by portions at room temperature. The reaction was allowed to proceed while stirring for one hours. The reaction mixture was concentrated under reduced pressure, and the concentrate was subjected to extraction with chloroform. Insoluble materials were filtered off, and the filtrate was washed with a dilute aqueous solution of hydrogen peroxide, then with water. The resulting solution was dried and concentrated to give colorless and clear syrup. Crystallization from aqueous alcohol gave 4-[3-(3-acetoxy-4-acetyl-2 propylphenoxy)propoxy]-3-bromobenzoic acid (2.0 g), m.p. 155°–156° C.

EXAMPLE 10

(1) A suspension of 4-acetoxy-3-bromobenzoic acid (1.5 g) in thionyl chloride (6 ml) was refluxed for one hour, followed by concentration to dryness. The residue was dissolved in toluene and the toluene was evaporated off. This procedure was carried out twice. The resulting oily substance was dissolved in acetone (10 ml), to which was added dropwise under ice-cooling 4-dimethylaminopropanol (0.8 ml). The mixture was stirred at room temperature for 30 minutes. The resulting crystals were collected by filtration, which were recrystallized from ethanolether to yield 3 -dimethylaminopropyl 4-acetoxy-3-bromobenzoate.hydrochloride (1.8 g) as colorless crystals, m.p. 163°–167° C.

(2) To a solution of 3-dimethylaminopropyl 4-acetoxy-3-bromobenzoate (380 mg) in methanol (4 ml) was added 2 N aqueous ammonia (0.75 ml). The reaction was allowed to proceed at room temperature for 15 minutes, then the solvent was evaporated off. The residue was crystallized from acetone and recrystallized from methanol-ether to give 3-dimethylaminopropyl 3-bromo-4-hydrochloride (200 mg) as colorless crystals, m.p. 186°–190° C.

(3) In dimethylformamide (30 ml), 3-(3-acetoxy-4-acetyl-2-propylphenoxy)propylbromide (1.6 g) was allowed to react with 3-dimethylaminopropyl 3-bromo-4-hydroxybenzoate.hydrochloride (1.7 g), potassium iodide (0.83 g) and potassium carbonate (0.7 g) at 60°–70° C. for 6 hours with stirring. Insoluble materials were filtered off, and the filtrate was concentrated. The resulting syrup was purified by means of a flash chromatography using silica-gel to give 3-dimethylaminopropyl 4-[3-(3-acetoxy-4-acetyl-2-propylphenoxy)propoxy]-3-bromobenzoate (1.8 g). The product was dissolved in ether, to which was added equivalent oxalic acid (250 mg) to give crystalline oxalate (1.8 g), m.p. 141°–142° C.

EXAMPLE 11

(1) In 60 ml of dichloromethane was dissolved 2.591 g of 4-acetoxy-3-bromobenzoic acid. After the addition of two drops of conc. sulfuric acid to the solution, isobutene was introduced into the mixture under ice-cooling for 30 minutes. The flask was stoppered tightly and kept standing for 2 days at room temperature. Nitrogen gas was introduced into the mixture so as to remove isobutene, and the resultant was washed with water, a saturated aqueous solution of sodium hydrogen carbonate, 1N hydrochloric acid and then water in the order mentioned. The resultant was dried with magnesium sulfate, and the solvent was removed by evaporation to give 2.55 g of brown oily product.

The oily product (1.9 g) was dissolved in 24 ml of ethanol, and 9 ml of 1N sodium hydroxide was added to the solution under stirring at room temperature. After the further stirring for one hour, the pH of the mixture was adjusted to 7 with acetic acid. Ethanol was removed by evaporation under reduced pressure and to the resultant was added water. The pH of the mixture was adjusted to 5 with acetic acid. The mixture was subjected to extraction with chloroform. The extract was dried with magnesium sulfate, and chloroform was removed by evaporation under reduced pressure. The resultant was subjected to purification with flash chromatography using silica gel, and subjected to recrystallization from hexane to give 0.76 g of tert-butyl 3-bromo-4-hydroxybenzoate as colorless needles. m.p. 106°–108° C.

(2) A mixture of 2,4-dihydroxy-3-propylacetophenone (85.5 g), anhydrous potassium carbonate (122 g), acetone (700 ml), and 1-bromo-3-chloropropane (87 ml) was refluxed for 8 hours under stirring, and cooled in an ice bath. An insoluble material was removed by filtration and washed with ethyl acetate (150 ml). The filtrate was evaporated to dryness and the residue was dissolved in dichloromethane (500 ml). N,N-Dimethylaminopyridine (0.5 g) and triethylamine (185 ml) were added to the ice-cooled solution. Then, to the solution was added dropwise acetic anhydride (125 ml) at 5°–10° C. and stirring was continued for 30 minutes. The ice-bath was removed and the solution was stirred at room temperature for 3 hours. Water (200 ml) was added to the solution keeping the temperature below 20° C., and the mixture was stirred at about 15° C. for 15 minutes. To the solution was added dichloromethane (300 ml) and water (300 ml).

The separated dichloromethane layer was washed with water (500 ml), dilute hydrochloric acid (500 ml), a saturated solution of sodium chloride in water (100 ml), in this order, and then dried (sodium sulfate). The solution was evaporated to dryness and the residue was distilled by the use of Kugelrohr (Aldrich, U.S.A.) to give 3-(3-acetoxy-4-acetyl-2-propylphenoxy)propyl chloride as yellow oil (132.5 g). b.p. 160°–220° C./1.2–1.5 mmHg.

NMR (CDCl$_3$)δ: 0.92(3H,t,J=7 Hz), ca.1.50(2H,m), 2.10–2.65(4H,m), 2.39(3H,s), 2.56(3H,s), 3.75(2H,t,J=6 Hz), 4.20(2H,t,J=6 Hz), 6.79(1H,d,J=9 Hz), 7.71(1H,d,J=9 Hz)

(3) To a mixture of 1.565 g of 3-(3-acetoxy-4-acetyl-2-propylphenoxy)propyl chloride, 375 mg of sodium iodide, 503 mg of sodium carbonate and 1.229 g of tert-butyl 3-bromo-4-hydroxybenzoate was added 10 ml of N,N-dimethylformamide, and the mixture was vigorously stirred at 80° to 85° C. for 6 hours. After cooling, to the reaction mixture was added 25 ml of ethyl acetate and 25 ml of water, and aqueous layer and organic layer were separated from each other.

The aqueous layer was subjected to extraction with 10 ml of ethyl acetate. The ethyl acetate layers were combined and dried with 25 ml of 2% hydrochloric acid and then with 25 ml of a saturated aqueous solution of NaCl. The solution was dried with sodium sulfate, and ethyl acetate was removed by evaporation under reduced pressure to give 3 g of tert-butyl 4-[3-(3-acetoxy-4-acetyl-2 propylphenoxy)propoxy]-3-bromobenzoate as pale brown oily product.

NMR (CDCl$_3$)δ: 0.88(3H,t,J=7 Hz), 1.32–1.70(2H,m), 1.57(9H,s), 2.20–2.65(4H,m), 2.33(3H,s), 2.45(3H,s), 4.13–4.40(4H,m), 6.78(1H,d,J=9 Hz), 6.86(1H,d,J=8 Hz), 7.67(1H,d,J=9 Hz), 7.88(1H,dd,J=2 and 8 Hz), 8.13(1H,d,J=2 Hz)

(4) In 10 ml of dioxane was dissolved 1.5 g of tert-butyl 4-[3-(3-acetoxy-4-acetyl-2-propylphenoxy)-propoxy]-3-bromobenzoate. To the solution was added under stirring at 20° C., 10 ml of a dioxane solution (2 N) of hydrogen chloride which was previously ice-cooled. The mixture was further stirred for 30 minutes at room temperature, and then to the mixture was added 10 ml of the dioxane solution of hydrogen chloride. The mixture was stirred for 1.5 hours, and concentrated under reduced pressure. The resultant was dissolved in 30 ml of chloroform, and the solution was washed with 30 ml of water and then dried over with magnesium sulfate. Chloroform was removed by evaporation under reduced pressure, and the resultant was dissolved in isopropyl ether. The solution was subjected to a treatment using activated charcoal, and to the solution was added hexane for crystallization. The crystals were collected by filtration, subjected to purification by silica gel column chromatography, and then recrystallized from aqueous ethanol to give 0.35 g of 4-[3-(3-acetoxy-4-acetyl 2-propylphenoxy)propoxy]-3-bromobenzoic acid as colorless crystals. m.p. 154°–156° C.

EXAMPLE 12

A mixture of 4-[3-(4-acetyl-3-hydroxy-2-propylphenoxy)propoxy]-3-fluorobenzoic acid (700 mg), dichloromethane (25 ml), triethylamine (2ml), acetic anhydride (2ml) and 4-dimethylaminopyridine (catalytic amount) was stirred at ice-cooling to room temperature for 6.5 hours. To the reaction mixture was added methanol (2ml), and the mixture was stirred for 30 minutes. After concentration, water was added to the residue. Solid materials were recovered by filtration and subjected to recrystallization from aqueous methanol to give crystals of 4-[3-(3-acetoxy-4-acetyl-2-propylphenoxy)propoxy]-3-fluorobenzoic acid (723 mg). m.p. 144°–145° C.

What we claim is:

1. A compound of the formula:

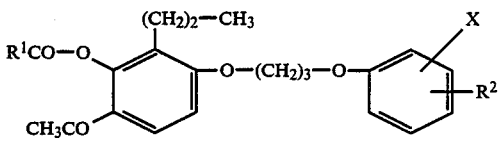

wherein R$^1$ stands for a lower alkyl group, R$^2$ stands for an optionally protected carboxyl group and X stands for a halogen or a salt thereof.

2. A compound as claimed in claim 1, wherein R$^1$ is methyl.

3. A compound as claimed in claim 1, wherein R$^2$ is carboxyl group.

4. A compound as claimed in claim 1, wherein R$^2$ is a group represented by the formula:

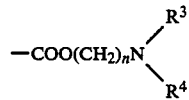

wherein n denotes an integer of 2 to 4, R$^3$ and R$^4$ independently stand for hydrogen or C$_{1-3}$ alkyl, and R$^3$ and R$^4$, taken together with the adjacent nitrogen atom, may form a 5- or 6-membered heterocyclic ring.

5. A compound as claimed in claim 1, wherein X is bromine.

6. A compound as claimed in claim 1, wherein the compound is 4-[3-(3-acetoxy-4-acetyl-2-propylphenoxy)propoxy]-3-bromobenzoic acid.

7. A compound as claimed in claim 1, wherein the compound is 3-(N,N-dimethylamino)propyl 4-[3-(4-acetyl-3-acetoxy-2-propylphenoxy)propoxy]-3-bromobenzoate.

8. A compound as claimed in claim 1, wherein the compound is 4-[3-(3-acetoxy-4-acetyl-2-propylphenoxy)propoxy]-3-chlorobenzoic acid.

9. A compound as claimed in claim 1, wherein the compound is 4-[3-(3-acetoxy-4-acetyl-2-propylphenoxy)propoxy]-3-fluorobenzoic acid.

10. A pharmaceutical composition for antagonizing the slow reacting substance of anaphylaxis which contains an effective antagonizing dose of a compound of the formula:

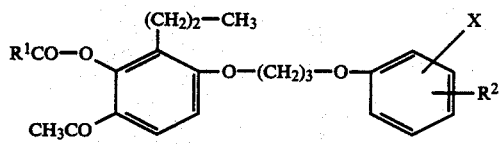

wherein $R^1$ stands for a lower alkyl group, $R^2$ stands for an optionally protected carboxyl group and X stands for a halogen or a salt thereof and a pharmaceutically acceptable carrier.

11. A method of antagonizing the slow reacting substance by administration to a mammal in need thereof of a compound of the formula:

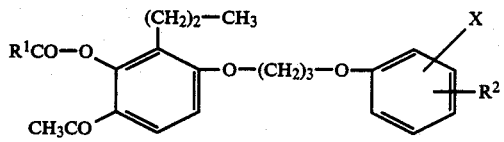

wherein $R^1$ stands for a lower alkyl group, $R^2$ stands for an optionally protected carboxyl group and X stands for a halogen or a salt thereof.

* * * * *